United States Patent
Minoguchi et al.

(10) Patent No.: US 8,840,598 B2
(45) Date of Patent: Sep. 23, 2014

(54) WRAPPER HAVING A TAB

(75) Inventors: Ryo Minoguchi, Cincinatti, OH (US); Ricky Alan Pollard, Moscow, OH (US); Letha Margie Hines, Cincinatti, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1380 days.

(21) Appl. No.: 11/900,571

(22) Filed: Sep. 12, 2007

(65) Prior Publication Data

US 2009/0069769 A1 Mar. 12, 2009

(51) Int. Cl.
| | | |
|---|---|---|
| A61F 13/34 | (2006.01) | |
| A61F 13/15 | (2006.01) | |
| B65D 65/28 | (2006.01) | |
| A61F 15/00 | (2006.01) | |
| A61F 13/551 | (2006.01) | |

(52) U.S. Cl.
CPC ......... *A61F 15/003* (2013.01); *A61F 13/55175* (2013.01); *A61F 13/34* (2013.01)
USPC .............. 604/385.18; 604/385.02; 229/87.05

(58) Field of Classification Search
CPC . A61F 13/003; A61F 13/34; A61F 13/55175; A61F 13/55185
USPC .............. 604/385.17–385.18, 904; 229/87.05
See application file for complete search history.

(56) References Cited

U.S. PATENT DOCUMENTS

| | | | |
|---|---|---|---|
| 2,499,414 A * | 3/1950 | Rabell | 604/377 |
| 2,679,349 A * | 5/1954 | Mullinix | 229/103.2 |
| 2,922,423 A * | 1/1960 | Rickard et al. | 604/14 |
| 3,013,558 A * | 12/1961 | Leupold | 604/377 |
| 3,358,686 A * | 12/1967 | Asaka | 604/14 |
| 3,520,302 A * | 7/1970 | Jones | 604/366 |
| 3,674,029 A | 7/1972 | Bates et al. | |
| 3,863,636 A * | 2/1975 | Johnson | 604/358 |
| 4,170,305 A | 10/1979 | Hull, Jr. et al. | |
| 4,648,513 A | 3/1987 | Newman | |
| 4,881,644 A | 11/1989 | Norquest et al. | |
| 5,133,457 A | 7/1992 | Kadel | |
| 5,180,059 A | 1/1993 | Shimatani et al. | |
| 5,287,960 A | 2/1994 | Kalb et al. | |
| 5,442,897 A | 8/1995 | Hinzmann et al. | |

(Continued)

FOREIGN PATENT DOCUMENTS

| | | |
|---|---|---|
| EP | 0 213 241 A1 | 8/1985 |
| EP | 0 597 446 B1 | 4/1998 |

(Continued)

OTHER PUBLICATIONS

PCT International Search Report dated Jun. 5, 2009.

*Primary Examiner* — Melanie Hand
*Assistant Examiner* — Paula L Craig
(74) *Attorney, Agent, or Firm* — Andrew J. Hagerty; Amanda T. Barry (57) ABSTRACT

Wrappers having one or more tabs are provided. The wrapper can have a first end, a second end, and a center portion disposed between the first end and the second end. The wrapper can include a first joined portion at the second end and a tab extending from the joined portion outwardly from the feminine device. In certain embodiments, at least a portion of the withdrawal member can extend through the joined portion into the tab.

16 Claims, 3 Drawing Sheets

(56) References Cited

U.S. PATENT DOCUMENTS

| | | |
|---|---|---|
| 5,471,820 A | 12/1995 | Oppe et al. |
| 5,988,386 A * | 11/1999 | Morrow ........................ 206/581 |
| 6,183,457 B1 * | 2/2001 | Kuhn ........................ 604/385.18 |
| 6,955,665 B2 | 10/2005 | Domeier et al. |
| 7,065,939 B2 | 6/2006 | Wasson et al. |
| 7,073,666 B2 | 7/2006 | Arndt |
| 2003/0220624 A1 * | 11/2003 | Domeier et al. ......... 604/385.02 |
| 2003/0220625 A1 | 11/2003 | Domeier et al. |
| 2004/0133142 A1 | 7/2004 | Lochte et al. |
| 2007/0156109 A1 * | 7/2007 | Loyd et al. ............... 604/385.02 |
| 2007/0239127 A1 * | 10/2007 | Bridges .................... 604/385.13 |

FOREIGN PATENT DOCUMENTS

| | | |
|---|---|---|
| EP | 0 807 075 B1 | 8/1999 |
| EP | 1 618 860 A1 | 1/2006 |
| EP | 1 639 974 A1 | 3/2006 |
| GB | 758879 | 10/1956 |
| WO | WO 03/082174 A1 | 10/2003 |

\* cited by examiner

WRAPPER HAVING A TAB

FIELD OF THE INVENTION

The invention relates to wrappers, and more particularly to wrappers having one or more tabs.

BACKGROUND OF THE INVENTION

Feminine devices, such as tampons and pessaries, are generally used by women within the vagina for feminine needs, such as, e.g., to absorb menstrual or other body exudates, for pelvic support, and/or for other feminine needs. Such feminine products can be inserted into the vagina by using an applicator, or can be inserted digitally, such as, e.g., by using a finger.

Feminine devices can be individually packaged. Individual packaging can improve hygiene, e.g., to keep the devices from being soiled by dust, unintended touching, and the like. Individual packaging includes wrappers, such as a wrapper made of plastic film, such as cellophane, polyethylene, and/or polypropylene. Digital tampons, for example, can be individually packaged in airtight wrappers that can assist in sustaining the shape of the enclosed tampon over time under possible changes of temperature and/or humidity, as well as facilitate ease of carrying the tampon before use. Such wrappers, however, can be difficult to remove from the tampon and can separate into smaller pieces during removal, which can be undesirable for many users.

As such, it would be desirable to provide a wrapper such as, e.g., a wrapper for a feminine device, with improved ease of removal.

SUMMARY OF THE INVENTION

Wrappers having one or more tabs are provided. The wrapper can have a first end, a second end, and a center portion disposed between the first end and the second end. The center portion can have a circumference substantially perpendicular to a longitudinal axis of the wrapper. The wrapper can include a first joined portion at the second end and a tab extending from the joined portion outwardly from the feminine device. In certain embodiments, at least a portion of the withdrawal member can extend through the joined portion into the tab. In addition, the wrapper can include at least one opening device provided along substantially the entire circumference, the opening device being adapted to substantially separate the wrapper into at least a first piece and a second piece upon deployment of the opening device, the first piece including the first end and the second piece including the second end.

DETAILED DESCRIPTION OF THE INVENTION

The present invention discloses a wrapper having a tab. The wrapper can at least partially enclose a feminine device, such as, e.g., a tampon or pessary. In certain embodiments, the feminine device can have a withdrawal member and the wrapper can include at least one tab that can enclose at least part of a withdrawal member of the device.

Preparing a feminine device for insertion can represent a major part of a user's experience with the device. Therefore, if the feminine device is difficult to prepare for insertion, such as, e.g., enclosed in a wrapper that can be difficult to remove, a user's experience can be adversely affected. Thus, wrappers of the present invention can provide improved removal of the wrapper from the device. In addition, or alternatively, such wrappers can provide improved deployment of the withdrawal member of the device prior to use. For example, digital tampons can include a withdrawal member that can be compacted, e.g., wound, looped, folded, entangled, or the like, when the tampon is contained in the wrapper. The withdrawal member can need to be deployed, e.g., stretched, straightened, loosened, unraveled, disentangled, or the like, by a user after wrapper removal and prior to insertion of the device. Grasping the withdrawal member and separating it from the wrapper can be awkward and can disrupt hygienic device handling due to the user touching the device with their fingers while the user tries to prepare the device. As such, wrappers of the present invention can provide an improved experience to a user, such as, e.g., by improving deployment of the withdrawal member and/or by improving the user's wrapper removal experience.

As used herein, the term "feminine device" includes devices useful for feminine needs, such as, e.g., incontinence articles and absorbent articles useful for feminine needs, such as articles that typically can be intended for feminine use internally, such as, e.g., within a user's vagina. Internal feminine devices can include, for example, tampons, pessaries, and contraceptive devices.

As used herein, the term "tampon" refers to any type of absorbent structure that can be inserted into the vaginal canal or other body cavity, such as, e.g., for the absorption of fluid, to aid in wound healing, and/or for the delivery of materials, such as moisture or active materials such as medicaments.

As used herein, the term "vaginal canal" refers to the internal genitalia of the human female in the pudendal region of the body. The terms "vaginal canal" or "within the vagina" as used herein are intended to refer to the space located between the introitus of the vagina (sometimes referred to as the sphincter of the vagina) and the cervix.

As used herein, "applicator" refers to a device or implement that facilitates the insertion of a feminine device, such as, e.g., a tampon or pessary, into an external orifice of a mammal, such as, e.g., the vaginal canal. Exemplary applicators include telescoping, tube and plunger, and compact applicators.

As used herein, the term "digital tampon" refers to a tampon that is intended to be inserted into a vagina with a user's finger and generally without aid of an applicator.

As used herein, the term "pessary" refers to any type of structure for the purpose of reducing urine leakage and/or supporting a prolapsed uterus and/or bladder. Such pessaries can have any variety of shapes and sizes including cylinder, ovate, spherical, tubular, annual rings, "U" shaped, cup shaped, rings, cubes or donut shaped, and can function in any suitable manner, such as, e.g., by direct application of support, lever force, expansion of the device by selection of material, and/or by inflation of the device.

As used herein, the term "wrapper" refers to a structure that can be formed of one or more wrapper materials and can at least partially enclose one or more devices, such as, e.g., a tampon and/or pessary, for packaging purposes. It can be constituted of one connected piece of one or more wrapper materials or it can be made from multiple pieces of one or more wrapper materials that can be joined together.

As used herein, the term "fixedly joined" refers to a connection that is not meant to be easily released, such as, e.g., a connection formed using a substantially permanent seal and/or a connection that cannot be unattached without at least partially destroying one of the attached components.

As used herein, the term "releasably joined" refers to a connection that is meant to be easily released.

As used herein, the term "insertion end" refers to the portion of the feminine device including the end that is intended to enter the vaginal canal first when inserting the feminine device into the vaginal canal.

As used herein, the term "withdrawal end" refers to the portion of the feminine device opposite the insertion end. In certain embodiments, the withdrawal end can include the end is intended to exit the vaginal canal first when the feminine device is removed from the vagina.

As used herein, the term "proximal end" refers to the end nearest the user's body during insertion of the device.

As used herein, the term "distal end" refers to the end furthest from the user's body during insertion of the device.

Figure 1:
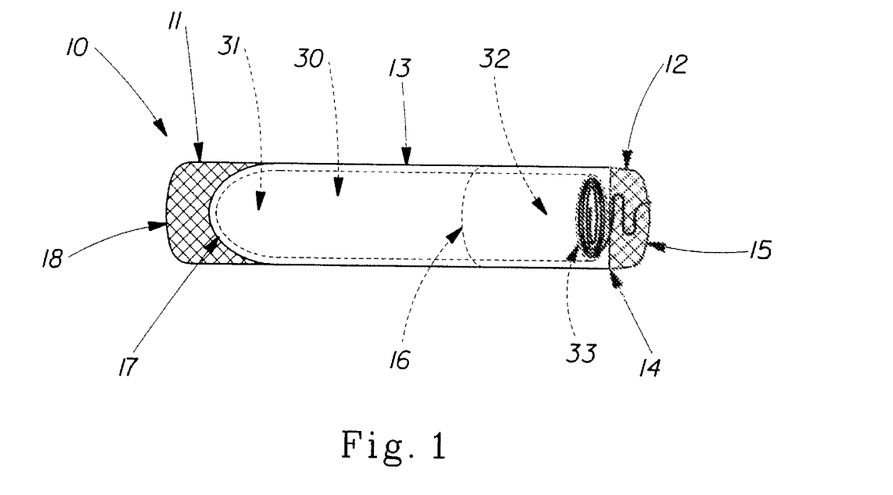
FIG. 1 is a perspective view of a wrapper of the present invention.

FIG. 1 shows one embodiment of a wrapper 10. The wrapper 10 has a first end 11, a second end 12, and a center portion 13 disposed between the first end and the second end. As shown in FIG. 1, the wrapper 10 can at least partially enclose a tampon 30. The tampon 30 can have an insertion end 31, a withdrawal end 32, and a withdrawal member 33. The wrapper can include a first joined portion 14 at the second end 12. In certain embodiments, the wrapper 10 can include a tab 15 extending from the first joined portion 14 outwardly from the tampon 30. At least a portion of the withdrawal member 33 can extend through the first joined portion 14 into the tab 15. The tab 15 can enclose at least a portion of the withdrawal member 33. As shown in FIG. 1, the wrapper 10 can have a second joined portion 17 at the first end 11. In certain embodiments, the wrapper 10 can have a second tab 18 extending from the second joined portion 17 outwardly from the tampon 30. The wrapper 10 can further include one or more opening devices 16, such as, e.g., a line of perforations as shown in FIG. 1. The opening device 16 can be disposed such that the user can separate the wrapper 10 into at least a first piece including the first end 11 and a second piece including the second end 12 upon deployment of the opening device 16, such as, e.g., by bending or twisting the wrapper 10.

Figure 2:
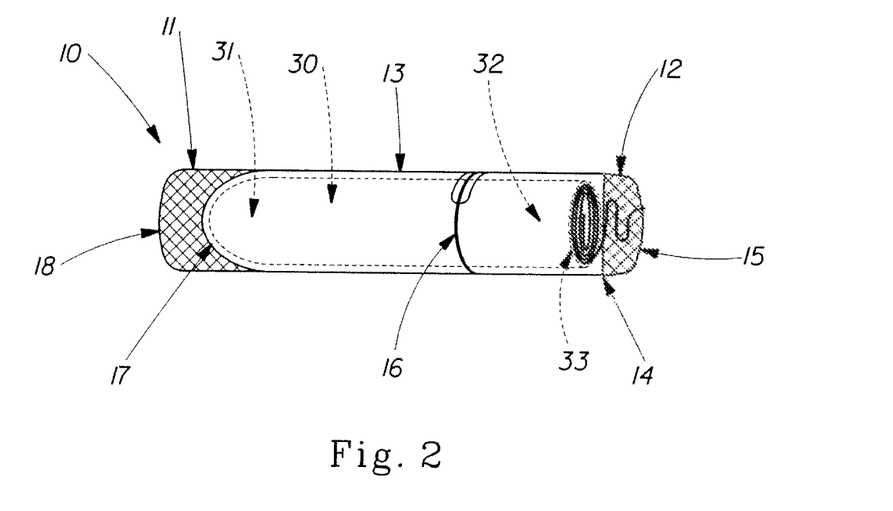
FIG. 2 is a perspective view of a wrapper of the present invention.

FIG. 2 shows one embodiment of a wrapper 10. The wrapper 10 has a first end 11, a second end 12, and a center portion 13 disposed between the first end and the second end. As shown in FIG. 2, the wrapper 10 can at least partially enclose a tampon 30. The tampon 30 can have an insertion end 31, a withdrawal end 32, and a withdrawal member 33. The wrapper can include a first joined portion 14 at the second end 12. In certain embodiments, the wrapper 10 can include a tab 15 extending from the first joined portion 14 outwardly from the tampon 30. At least a portion of the withdrawal member 33 can extend through the first joined portion 14 into the tab 15. The tab 15 can enclose at least a portion of the withdrawal member 33. As shown in FIG. 2, the wrapper 10 can have a second joined portion 17 at the first end 11. In certain embodiments, the wrapper 10 can have a second tab 18 extending from the second joined portion 17 outwardly from the tampon 30. The wrapper 10 can further include one or more opening devices 16. As shown in FIG. 2, wrapper 10 includes a tear tape as an opening device 16. The user can remove the wrapper 10 by removing the tear tape 16 and can deploy the withdrawal member 33 by grasping and pulling tab 15 at the second end 12.

Figure 3:
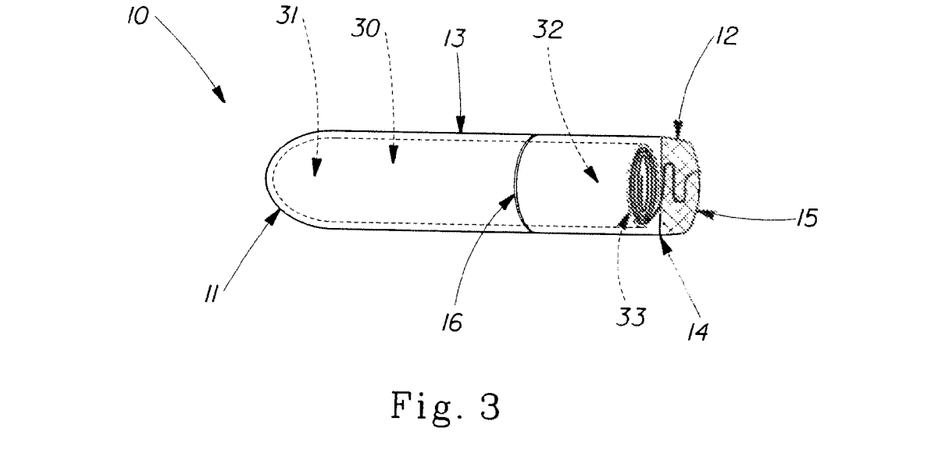
FIG. 3 is a perspective view of a wrapper of the present invention.

FIG. 3 shows one embodiment of a wrapper 10. The wrapper 10 has a first end 11, a second end 12, and a center portion 13 disposed between the first end and the second end. As shown in FIG. 3, the wrapper 10 can at least partially enclose a tampon 30. The tampon 30 can have an insertion end 31, a withdrawal end 32, and a withdrawal member 33. The wrapper can include a first joined portion 14 at the second end 12. In certain embodiments, the wrapper 10 can include a tab 15 extending from the first joined portion 14 outwardly from the tampon 30. At least a portion of the withdrawal member 33 can extend through the first joined portion 14 into the tab 15. The tab 15 can enclose at least a portion of the withdrawal member 33. The wrapper 10 can further include one or more opening devices 16, such as, e.g., a seal line as shown in FIG. 3. The opening device 16 can be disposed such that the user can separate the wrapper 10 into at least a first piece including the first end 11 and a second piece including the second end 12 upon deployment of the opening device 16, such as, e.g., by bending or twisting the wrapper 10.

Figure 4:
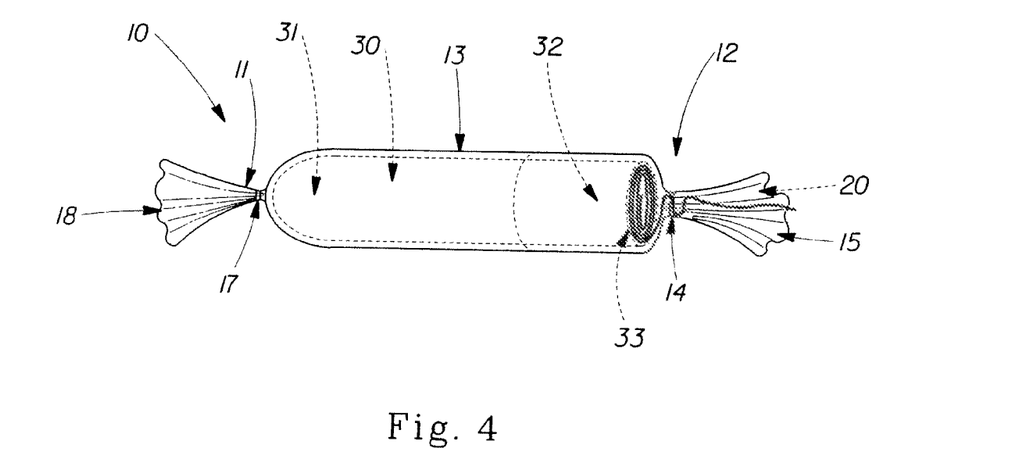
FIG. 4 is a perspective view of a wrapper of the present invention.

FIG. 4 shows one embodiment of a wrapper 10. The wrapper 10 has a first end 11, a second end 12, and a center portion 13 disposed between the first end and the second end. The wrapper 10 can at least partially enclose a tampon 30. The tampon 30 can have an insertion end 31, a withdrawal end 32, and a withdrawal member 33. The wrapper can include a first joined portion 14 at the second end 12. The wrapper 10 can include a tab 15 extending from the first joined portion 14 outwardly from the tampon 30. In certain embodiments, the joined portion 14 can be formed by twisting, crimping, and/or gathering the wrapper 10. As shown in FIG. 4, the tab 15 can have an outer surface 19 that can define an interior space 20. At least a portion of the withdrawal member 33 can extend through the first joined portion 14 into the interior space 20. As shown in FIG. 4, the wrapper 10 can have a second joined portion 17 at the first end 11. In certain embodiments, the wrapper 10 can have a second tab 18 extending from the second joined portion 17 outwardly from the tampon 30. The wrapper 10 can further include one or more opening devices 16. The opening device 16 can be disposed such that the user can separate the wrapper 10 into at least a first piece including the first end 11 and a second piece including the second end 12 upon deployment of the opening device 16, such as, e.g., by bending or twisting the wrapper 10.

Figure 5:
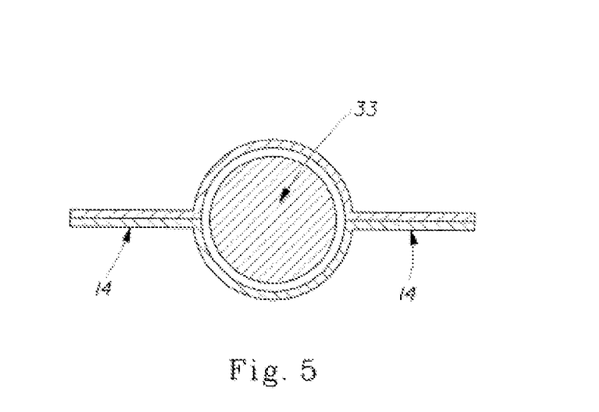
FIG. 5 is a cross-sectional view of a wrapper of the present invention.

FIG. 5 shows a cross-sectional view of a wrapper 10 along a joined portion 14 at the second end 12. The withdrawal member 33 can be associated with the joined portion 14 without being joined to the wrapper 10. As shown in FIG. 5, the joined portion 14 can be provided on either side of the withdrawal member 33.

Figure 6:
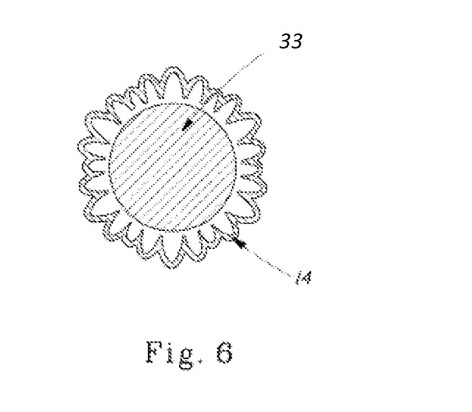
FIG. 6 is a cross-sectional view of a wrapper of the present invention.

FIG. 6 shows a cross-sectional view of a wrapper 10 along a joined portion 14 at the second end 12. The withdrawal member 33 can be associated with the joined portion 14 without being joined to the wrapper 10. As shown in FIG. 6, the wrapper 10 can be gathered to form a joined potion 14 around the withdrawal member 33 without joining the withdrawal member 23 to the wrapper 10. Alternatively, the wrapper 10 can be gathered to form joined portion 14 and the withdrawal member 33 can be joined to the joined portion 14 and/or to the tab 15.

In certain embodiments, the wrapper can separate into two or more pieces, for example, at least a piece covering the withdrawal end of the enclosed feminine device and/or a piece covering at least a portion of the insertion end of the device. In addition or alternatively, the wrapper can be designed such that it opens to allow the withdrawal end of the device to be exposed while other portions of the device remain substantially enclosed in the wrapper. In certain embodiments, the user can open the wrapper adjacent to the withdrawal end of the feminine device to deploy the withdrawal member while the insertion end of the device remains wrapped. The user can hygienically hold the wrapped portion of the feminine device while the deploying the withdrawal member and preparing the device for insertion. For example, in certain embodiments, the user can remove the wrapper and deploy the withdrawal member by grasping the wrapper adjacent the insertion end of the feminine device and then grasping and pulling the tab positioned near the withdrawal end of the device, breaking the opening device and separating the wrapper into at least two pieces. At least the insertion end of the device can be retained within a piece of the wrapper. In certain embodiments, the withdrawal member can be extended when the user pulls the tab at the withdrawal end of the device to open the wrapper. Once the withdrawal member is deployed, the user can release the tab, which can allow the withdrawal member to separate from the tab. The user can then remove the rest of the wrapper from the insertion end of the feminine device.

The withdrawal member can be associated with the tab in any suitable manner, such as, e.g., fixedly joined, releasably joined, and/or associated without being joined to the wrapper. For example, in certain embodiments, the wrapper can be releasably joined to the wrapper, such as, e.g., releasably joined to the tab and/or joined portion such that the withdrawal member is intended to be dissociated from the tab and/or joined portion prior to use of the device. Alternatively, the withdrawal member can be associated with the wrapper in a manner that does not connect the withdrawal member to the wrapper, such as, e.g., by enclosing a portion of the withdrawal member within a joined portion of the wrapper without attaching the withdrawal member to the joined portion. For example, the withdrawal member can extend through the joined portion into the withdrawal member and the joined portion can hold the withdrawal member in place within the tab prior to deployment of the withdrawal member. In certain embodiments, the withdrawal member can be associated with by wrapper by extending through the joined portion such that the withdrawal member potentially has substantially free movement in a longitudinal direction. In addition, or alternatively, the withdrawal member can be associated with the wrapper by extending through the joined portion such that the withdrawal member has restricted movement in a direction perpendicular to the longitudinal direction.

In certain embodiments, the withdrawal member can be associated with the wrapper in a manner that does not connect the withdrawal member to the wrapper and the withdrawal member can extend into and/or through the tab. In addition, the wrapper can be configured such that when the user grasps the tab to prepare the device for insertion, the user grasps the tab and the withdrawal member. Thus, when the user pulls the tab to open the wrapper, the user also can extend the withdrawal member. In certain embodiments, when the user releases the tab, the user can also release the withdrawal member, which can easily separate from the tab, such as, e.g., by dissociating from the tab without any external force applied by the user.

The wrapper can include any suitable opening device. Suitable opening devices include, e.g., one or more perforations, such as, e.g., disclosed in U.S. Pat. No. 6,955,665, one or more depressions, such as, e.g., disclosed in European Patent No. EP 597446, a tear tape, a line of sealing, such as, e.g., disclosed in U.S. Pat. No. 4,648,513, and the like. In certain embodiments, the one or more opening devices can be provided around at least a portion of a perimeter or a length of the wrapped feminine device.

The wrapper material used can be any material suitable for use for wrapping a feminine device. Suitable wrapper materials include, e.g., plastic films made of cellophane, polyethylene, polypropylene, polyester, polystyrene, PET (polyethylenetherephthalate), polyamide, polyvinylchloride, ethylene-vinyl acetate copolymer and the like; synthetic or natural elastomers, e.g., rubber; generally occlusive materials such as metallic foils, e.g., aluminum foil; non-occlusive or porous materials, such as nonwoven materials, woven materials, scrims, meshes, and papers; or any other suitable materials. In certain embodiments, the wrapper can include one or more flexible polymeric films, such as, for example, films having a thickness of less than about 1 mm.

The wrapper can be made using any suitable technique, including, for example, heat-shrinking, heat sealing, adhesives, pressure, stretching, lamination, coating, gluing, embossing, crimping, sewing, stitching, entangling, mechanical interlocking, cold pressure welding, ultrasonic bonding, and/or combinations thereof.

In certain embodiments, the wrapper material tightly conforms to the outer surface of the wrapped tampon. This can be particularly well achieved by using heat-shrinkable or stretchable materials as wrapper material. 'Tightly conforming' of the wrapper to the outer surface of the wrapped tampon as used herein means that there is substantially no visually noticeable void space between the wrapper and the tampon. In other words, the perimeter of the tightly conforming wrapper on average exceeds the perimeter of the outer surface of the tampon by about 50%, about 30%, about 10% or even about 5%. Since the perimeter of a tampon can typically change as a function of the length of said tampon, especially because the tampon has often an insertion end with a tip or has tails or indents in its outer surface, the aforementioned limits for the tight conformation of the wrapper apply to at least all substantially lengthwise portions of the outer surface of the tampon, and in some embodiments, to all portions of the outer surface of the tampon. In some embodiments, of the present invention some regions of the wrapper material may provide additional functional benefits, such as cord deployment means. In these regions the wrapper material may not tightly conform to the outer surface of the tampon according to the definition herein. However, according to the present invention the wrapper material tightly conforms to the lengthwise portions of the outer surface of the tampon by at least about 70%, about 80% or even at least about 90% to the lengthwise portions of the outer surface of the tampon. As an example, the aforementioned perimeters of the wrapper and the tampon can be measured along the length of the tampon in steps of every 10% of the length of the tampon.

As set forth herein, the wrapper can include one or more tabs. Suitable tabs include, e.g., tabs set forth in, e.g., U.S. Pat. Nos. 4,648,513; 5,133,457; and 6,955,665. In certain embodiments, the wrapper can comprise a tab in a piece of the wrapper disposed adjacent the withdrawal end of the enclosed feminine device. In certain embodiments, the wrapper can comprise a tab in a piece of the wrapper covering the withdrawal end of the enclosed device and a tab in a piece of the wrapper covering the insertion end of the enclosed device. By holding and pulling the tab, the user can easily remove the wrapper from the device after opening the wrapper by the opening means. The tab can comprise a texture, an embossing, an adhesive, or the like, on one or more surfaces for secure grip of the tab. A tab of a wrapper of the present invention can have any suitable shape, such as e.g., a flap, a strip, a cord, a twist, a flare, a frill, a fringe, a ribbon, a loop, or the like. It can be constructed as part of the wrapper material and/or by attaching an additional material to the wrapper. It can be formed using any suitable technique, including, for example, pressing, heat sealing, adhesives, gluing, lamination, embossing, crimping, sewing, stitching, entangling, raveling, twisting, folding, mechanical interlocking, welding, ultrasonic bonding, fusing, and/or combinations thereof.

The tab can have any suitable size. Suitable sizes include, for example, greater than about 5 mm long by greater than about 10 mm wide, such as, e.g., greater than about 10 mm long by greater than about 20 mm wide, such as, e.g., from about 5 mm to about 20 mm long by about 10 mm to about 30 mm wide, or any other suitable size. In certain embodiments, the tab can be large enough for the user to recognize and handle it easily. In addition, or alternatively, the tab can be printed such that the user can recognize it easily.

In certain embodiments, the tab can enclose, bind, sandwich, envelope, or otherwise contain, at least a portion of a withdrawal member of the feminine device. The tab can enclose a portion of the withdrawal member in any suitable manner. In certain embodiments, the tab can enclose a portion of the withdrawal member without substantial bonding between the withdrawal member and the tab, such as, e.g., without substantial gluing or fusing.

The feminine device can have a withdrawal member. The withdrawal member can be any suitable configuration, such as, e.g., one or more cords, strings, finger covers, ribbons, an extension of a material of the device, or combinations thereof. The withdrawal member can be made of any suitable material, such as, e.g., cotton and rayon. The withdrawal member can optionally be provided with a secondary absorbent member. Suitable secondary absorbent members are described in, e.g., U.S. Pat. No. 6,258,075.

In certain embodiments, the feminine device can be a tampon. The tampon can include a pledget that can include a single material or a combination of materials. The materials for the tampon can be formed into a fabric, web, or batt that is suitable for use in the tampon by any suitable process such as, for example, airlaying, carding, wetlaying, hydroentangling, or other known techniques. The tampon can be any suitable tampon, such as, e.g., a digital tampon and/or an applicator tampon.

The pledget can be constructed from a wide variety of liquid-absorbing materials commonly used in absorbent articles. Such materials include, for example, rayon (such as GALAXY rayon (a tri-lobed rayon) or DANUFIL rayon (a round rayon), both available from Kelheim Fibres GmbH of Kelheim, Germany), cotton, folded tissues, woven materials, nonwoven materials, synthetic and/or natural fibers or sheeting, comminuted wood pulp, which is generally referred to as airfelt, foams, or combinations of these materials. Examples of other suitable materials include: creped cellulose wadding; meltblown polymers including coform; chemically stiffened, modified or cross-linked cellulosic fibers; synthetic fibers such as crimped polyester fibers; peat moss; foam; tissue including tissue wraps and tissue laminates; or any equivalent material or combinations of materials, or mixtures of these. Additionally, superabsorbent materials, such as superabsorbent polymers or absorbent gelling materials can be incorporated into the tampon.

The pledget can have any suitable shape, size, material, or construction prior to compression and/or shaping. For example, the pledget can include a rolled, tubed, or flat construction of an absorbent that can be a circle, an oval, a semi-circle, a triangle, a chevron shape, an H shape, a bow-tie shape, or any other suitable shape, such as, e.g., shapes described in, for example, U.S. Pat. Nos. 3,738,364; 5,911,712; 6,740,070; 6,887,266; and 6,953,456.

In certain embodiments, all or a portion of the tampon can be compressed into a substantially cylindrical configuration, however, other shapes are possible. These can include shapes having a cross section or cross-section element that can be described as rectangular, triangular, trapezoidal, semi-circular, hourglass, or other suitable shapes. In certain embodiments, the tampon can have a radially compressed rolled construction. The tampon can be constructed by rolling and radially compressing a pledget. In addition, or alternatively, the tampon can include an asymmetric insertion end, such as, e.g., tampons disclosed in U.S. patent application Ser. Nos. 11/526,041 and 11/525,513.

A tampon can comprise one or more overwraps. The overwrap can be any suitable material, such as, for example, rayon, cotton, bicomponent fibers, polyethylene, polypropylene, other suitable natural or synthetic fibers known in the art, and mixtures thereof. In certain embodiments, the tampon can comprise an overwrap material that substantially encloses the compressed tampon. In certain embodiments, the overwrap can extend from the withdrawal end of the tampon.

In certain embodiments, the tampon can include a finger pocket and/or a finger indent at the withdrawal end of the tampon, such as, e.g., to aid in insertion described in, such as, e.g., U.S. Pat. No. 6,283,952. In certain embodiments, at least a portion of the withdrawal member can be at least partially disposed in the finger pocket and/or the finger indent. The finger pocket or the finger indent may be hidden in the finished tampon and appear once the user prepares the device for insertion at least partially extending the withdrawal member, and/or loosening the withdrawal end of the tampon by moving the withdrawal cord. In addition, or alternatively, the tampon can include an overwrap that extends from the withdrawal end and forms a finger cover. In certain embodiments, the tampon can include an overwrap that extends from the withdrawal end and forms an absorbent skirt. In addition, the excess of the overwrap can be at least partially disposed in a finger pocket or a finger indent and can be pulled out to provide a finger cover or an absorbent skirt when the user prepares the tampon for insertion. In certain embodiments, the excess of the overwrap can be joined with the withdrawal cord and disposed in the finger pocket or the finger indent along with the withdrawal cord, such as, for example, in U.S. patent application Ser. Nos. 11/525,553 and 11/525,730.

In certain embodiments, the tampon can be inserted using an applicator. Any suitable applicator can be used, including, e.g., tube and plunger type arrangements that can be plastic, paper, or other suitable material, and compact type applicators. In certain embodiments, the applicator allows the user to better perceive the shape of the tampon, such as, e.g., an applicator comprising translucent and/or transparent materials, and/or an applicator comprising an insertion end that follows and/or otherwise displays the shape of the enclosed tampon. In certain embodiments, the tampon can be inserted using an applicator wherein the applicator includes an insertion end that is formed to be asymmetric around a longitudinal axis of the applicator. The tampon can also be inserted using an applicator that comprises an insertion end that is exposed such that the asymmetric insertion end of the tampon is visible.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A feminine device comprising an insertion end, a withdrawal end, and a withdrawal member, the withdrawal member having a proximal end nearest the withdrawal end of the feminine device and a distal end disposed opposite the proximal end,
the feminine device being at least partially enclosed by at least one wrapper comprising a wrapper material,
the wrapper comprising a first end disposed adjacent to the insertion end, a second end disposed adjacent the withdrawal end, and a center portion disposed between the first end and the second end,
the center portion having a circumference substantially perpendicular to a longitudinal axis of the wrapper,
the wrapper material being twisted, crimped, or gathered to form a first joined portion at the second end, and a tab extending from the joined portion outwardly from the feminine device,
the tab having an outer surface and being adapted to be held and pulled by a user, wherein at least a portion of the withdrawal member extends through the joined portion into the tab, the tab enclosing at least a portion of the withdrawal member, and
wherein the wrapper includes an opening device that is a line of perforations provided along the entire circumference, the opening device being adapted to separate the wrapper into at least a first piece and a second piece upon deployment of the opening device, the first piece including the first end and the second piece including the second end.

2. The feminine device of claim 1, wherein the tab encloses at least a portion of the distal end of the withdrawal member.

3. The feminine device of claim 1, wherein the outer surface comprises a first surface and a second surface disposed opposite the first surface, the first surface comprising a first material and the second surface comprising a second material, the first material and the second material being the same or different, and wherein at least a portion of the withdrawal member is disposed between the first material and the second material.

4. The feminine device of claim 1, wherein the tab includes at least one texture, at least one embossment, and/or at least one adhesive on at least a portion of the outer surface.

5. The feminine device of claim 1, wherein the withdrawal member is not joined to the joined portion.

6. The feminine device of claim 1, wherein the withdrawal member is not joined to the tab.

7. The feminine device of claim 1, wherein the withdrawal member is releasably joined to the tab.

8. The feminine device of claim 1, wherein the tab is from about 5 mm to about 20 mm long by about 10 mm to about 30 mm wide.

9. The feminine device of claim 1, wherein the feminine device is a digital tampon having an outer surface, and the first end, second end, and center portion of the wrapper tightly conforms to the outer surface of the tampon.

10. The feminine device of claim 1, wherein the wrapper includes a second joined portion at the first end and a second tab extending from the second joined portion outwardly from the feminine device.

11. A feminine device comprising an insertion end, a withdrawal end, and a withdrawal member, the withdrawal member having a proximal end nearest the withdrawal end of the feminine device and a distal end disposed opposite the proximal end,
the feminine device being at least partially enclosed by at least one wrapper comprising a wrapper material, the wrapper comprising a first end disposed adjacent to the insertion end, a second end disposed adjacent the withdrawal end, and a center portion disposed between the first end and the second end, the center portion having a circumference substantially perpendicular to a longitudinal axis of the wrapper,
the wrapper material being twisted, crimped, or gathered to form a first joined portion at the second end and a tab extending from the joined portion outwardly from the feminine device,
the tab having an outer surface and being adapted to be held and pulled by a user, the outer surface defining an interior space,
wherein at least a portion of the withdrawal member extends through the joined portion into the interior space,
wherein the wrapper includes an opening device that is a line of perforations provided along the entire circumference, the opening device being adapted to separate the wrapper into at least a first piece and a second piece upon deployment of the opening device, the first piece including the first end and the second piece including the second end.

12. The feminine device of claim 11, wherein the feminine device is a tampon or pessary.

13. The feminine device of claim 11, wherein the wrapper includes a second joined portion at the first end and a second tab extending from the second joined portion outwardly from the feminine device.

14. A digital tampon comprising an outer surface, an insertion end, a withdrawal end, and a withdrawal member, the withdrawal member having a proximal end nearest the withdrawal end of the digital tampon and a distal end disposed opposite the proximal end,
the digital tampon being enclosed by at least one wrapper comprising a wrapper material that conforms to the outer surface of the tampon,
the wrapper comprising a first end disposed adjacent to the insertion end, a second end disposed adjacent the withdrawal end, and a center portion disposed between the first end and the second end,
the center portion having a circumference substantially perpendicular to a longitudinal axis of the wrapper, the center portion having an opening device that is a line of perforations provided along substantially the entire circumference, the opening device being adapted to separate the wrapper into at least a first piece and a second piece upon deployment of the opening device, the first piece including the first end and the second piece including the second end, the wrapper material being twisted, crimped, or gathered to form a first joined portion at the second end and a tab extending from the joined portion outwardly from the digital tampon, the tab having an outer surface, wherein at least a portion of the withdrawal member extends through the joined portion into the tab, the tab enclosing at least a portion of the withdrawal member.

15. The tampon of claim 14, wherein the wrapper includes a second joined portion at the first end and a second tab extending from the second joined portion outwardly from the digital tampon.

16. The tampon of claim 14, wherein the tab is from about 5 mm to about 20 mm long by about 10 mm to about 30 mm wide.

* * * * *